A picture containing text

Description automatically generated

(12) United States Patent
Chao et al.

(10) Patent No.: US 7,179,619 B2
(45) Date of Patent: Feb. 20, 2007

(54) METHODS AND COMPOSITIONS FOR INHIBITING HERPESVIRAL REPLICATION

(75) Inventors: Sheng-Hao Chao, Vienna, VA (US); Jeremy S. Caldwell, La Jolla, CA (US)

(73) Assignee: IRM LLC, Hamilton (BM)

( * ) Notice: Subject to any disclaimer, the term of this patent is extended or adjusted under 35 U.S.C. 154(b) by 170 days.

(21) Appl. No.: 10/885,862

(22) Filed: Jul. 7, 2004

(65) Prior Publication Data

US 2005/0058991 A1    Mar. 17, 2005

Related U.S. Application Data

(60) Provisional application No. 60/486,134, filed on Jul. 10, 2003.

(51) Int. Cl.
*C12P 21/06* (2006.01)
(52) U.S. Cl. ............................ 435/69.1; 435/6; 435/7.1
(58) Field of Classification Search .................... 435/6, 435/69.1, 7.1, 5
See application file for complete search history.

(56) References Cited

OTHER PUBLICATIONS

Swift et al, Molecular and Cellular Biology, 1998, vol. 18, No. 9, pp. 5109-5120.*
PCT International Search Report mailed on Jan. 7, 2005 for International Application No. PCT/US2004/22341.
Meier et al. Requirement of Multiple cis-Acting Elements in the Human Cytomegalovirus Major Immediate-Early Distal Enhancer for Viral Gene Expression and Replication. Journal of Virology, Jan. 2002, vol. 76, No. 1, pp. 313-326.
Lundquist et al. A Strong Negative Transcriptional Regulatory Region between the Human Cytomegalovirus UL127 Gene and the Major Immediate-Early Enhancer. Journal of Virology, Nov. 1999, vol. 73, No. 11, pp. 9039-9053.
Isomura et al. The Human Cytomegalovirus Major Immediate-Early Enhancer Determines the Efficiency of Immediate-Early Gene Transcription and Viral Replication In Permissive Cells at Low Multiplicity of Infection. Journal of Virology, Mar. 2003, vol. 77, No. 6, pp. 3602-3614.
Macias et al. Cellular or Viral Protein Binding to a Cytomegalovirus Promoter Transcription Initiation Site: Effects on Transcription. Journal of Virology, Jun. 1996, vol. 70, No. 6, pp. 3628-3635.
Lashmit et al. Cellular Repressor Inhibits Human Cytomegalovirus Transcription from the UL127 Promoter. Journal of Virology, May 2004, pp. 5113-5123.
Lu et al., Endocrinology 137: 2959-2967, 1996.

* cited by examiner

*Primary Examiner*—Ali R. Salimi
(74) *Attorney, Agent, or Firm*—Timothy L. Smith; Genomics Institute of the Novartis Research Foundation

(57) ABSTRACT

This invention provides methods of screening for compounds that inhibit herpesviral transcription and replication. The methods comprise screening test compounds for ability to enhance the activity of homeodomain transcription factor PDX1 in repressing transcription of herpesviral genes (e.g., the IE gene of cytomegalovirus). Transcriptional repression by PDX1 can be monitored using an expression vector comprising a reporter gene operably linked to a PDX1-binding, upstream transcription regulatory sequence of the herpesvirus. The invention further provides methods and pharmaceutical compositions for stimulating PDX1-mediated transcriptional repression in a subject and for treating diseases and conditions associated with herpesviral infection.

9 Claims, 6 Drawing Sheets

METHODS AND COMPOSITIONS FOR INHIBITING HERPESVIRAL REPLICATION

CROSS-REFERENCE TO RELATED APPLICATIONS

This application claims the benefit of priority under 35 U.S.C. §119(e) to U.S. Provisional Patent Application No. 60/486,134, filed Jul. 10, 2003. The disclosure of the priority application is incorporated herein by reference in its entirety and for all purposes.

FIELD OF THE INVENTION

This invention relates to the discovery that the transcription factor PDX1 plays an important role in repressing transcription of the immediate early (IE) gene of cytomegalovirus (CMV). The invention accordingly provides methods for identifying novel compounds that enhance the transcription repressing activity of PDX1. Such novel modulators can be used to modulate PDX1-mediated transcriptional repression of herpesviral genes and to inhibit replication of herpesviruses, e.g., CMV.

BACKGROUND OF THE INVENTION

Members of the herpesviridae family are enveloped, double-stranded DNA viruses with relatively large complex genomes. At least 8 human herpesviruses have been identified, including human herpesvirus 1,2 (HSV-1, HSV-2), varicellovirus (VZV) or human herpesvirus 3, cytomegalovirus (CMV) or human herpesvirus 5, roseolovirus or human herpesvirus 6,7 (HHV-6, HHV-7), lymphocryptovirus (Epstein-Barr virus or EBV) or human herpesvirus 4, and rhadinovirus or human herpesvirus 8. These viruses are implicated in a number of human diseases such as facial or genital lesions and lynphotropic conditions. Human herpesvirus infections are endemic, and sexual contact is a significant method of transmission for several herpesviruses including herpes simplex virus 1 and 2, human CMV and likely Karposi's sarcoma herpesvirus. Prevalence of genetial herpes and corresponding rise of neonatal infection have implicated Epstein-Barr virus and Karposi's sarcoma herpesvirus as cofactors in human cancers.

Among herpesviruses, human CMV is a significant opportunistic pathogen responsible for serious clinical consequences in a variety of human subjects. Human subjects affected by CMV include immunosuppressed patient groups such as neonate and infants, persons with AIDS and individuals undergoing immunosuppressive regimes for the purpose of organ or bone marrow transplantation. Like other human herpesviruses, CMV establishes a life-long latent infection with its human host and is ubiquitous in the population with upwards of 75% infectivity rate found in the United States.

The currently available drugs for treating infections of herpesviruses are not very satisfactory due to various reasons. There is a need in the art to identify alternative drug targets and better agents to treat diseases and conditions associated with herpesviruses, e.g., CMV infection. The instant invention fulfills this and other needs.

SUMMARY OF THE INVENTION

This invention provides novel methods for identifying modulators that inhibit transcription and replication of herpesviruses. Such modulators can be used, e.g., in the treatment of human herpesviral infections, e.g., CMV infection.

In one aspect, the invention provides methods of identifying compounds that inhibit replication of a herpesvirus that infects human cells. The methods entail screening test compounds for ability to enhance PDX1-mediated repression of gene transcription of the herpesvirus. In some methods, the screening is carried out by contacting the test compounds with a PDX1 polypeptide and a gene under the control of a PDX1 response element, followed by comparing expression level of the gene in the presence of the test compounds to expression level of the gene in the absence of the test compound. In some of these methods, expression level of the gene is measured using a reporter construct comprising the PDX1 response element operably linked to a polynucleotide that encodes a detectable label.

In some of the methods, the PDX1 response element comprises an upstream transcription regulatory sequence from the IE gene of the herpesvirus. In some of these methods, the herpesvirus is human cytomegalovirus (CMV), and the PDX1 polypeptide is human PDX1. The transcription regulatory sequence can comprise nucleotides −593 to −549 of the IE gene of human CMV (SEQ ID NO: 1).

In some of the methods, the test compounds are pre-screened for ability to specifically bind to the PDX1 polypeptide. Some of the methods further comprise testing the identified compounds for ability to inhibit replication of the herpesvirus.

In a related aspect, the invention provides methods of identifying a compound that inhibits replication of a herpesvirus that infects human cells. The methods entails contacting a test compound, a PDX1 polypeptide, and a reporter gene operably linked to a PDX1 response element, and then comparing expression level of the reporter gene in the presence of the test compound to expression level of the reporter gene in the absence of the test compound. In some of the methods, the PDX1 response element comprises a transcription regulatory sequence from the IE gene of the herpesvirus. In some of these methods, the herpesvirus is human CMV, and the PDX1 response element comprises nucleotides −593 to −549 of the upstream regulatory region of human CMV IE gene (SEQ ID NO: 1).

In some of the methods, the reporter gene and the PDX1 response element are present in an expression vector. In some of the methods, the contacting is in a host cell expressing the PDX1 polypeptide. In some other methods, the PDX1 polypeptide is expressed from a second expression construct that has been introduced into the host cell. In some of the methods, the reporter gene is a luciferase gene. In some methods, the host cell is HEK 293 cell.

In another aspect, the invention provides methods of inhibiting replication of a herpesvirus in a human subject. The methods entail administering to the subject a pharmaceutical composition comprising an effective amount of a compound that inhibits replication of the herpesvirus. The compound is identified by screening test compounds for ability to enhance PDX1-mediated repression of transcription of genes of the herpesvirus. Some of these methods are directed to inhibiting replication of human CMV.

A further understanding of the nature and advantages of the present invention may be realized by reference to the remaining portions of the specification and claims.

(A) Diagram of the promoter-enhancer region of human CMV IE genes. The locations of the transcription start sites (+1), enhancer (−118 to −524), as well as the 45-nucleotide region of interest (−549 to −593; SEQ ID NOs: 1 and 2) are indicated. The putative binding motifs for homeobox proteins are underlined. (B) Alignment of the first 11 nucleotides of the 45-bp CMV DNA (SEQ ID NO: 3) and Ela1 B element (SEQ ID NO: 4) that associates with PBX-MEIS-PDX trimers. A solid line indicates identity and a dashed line indicates similarity.

Figure 2:
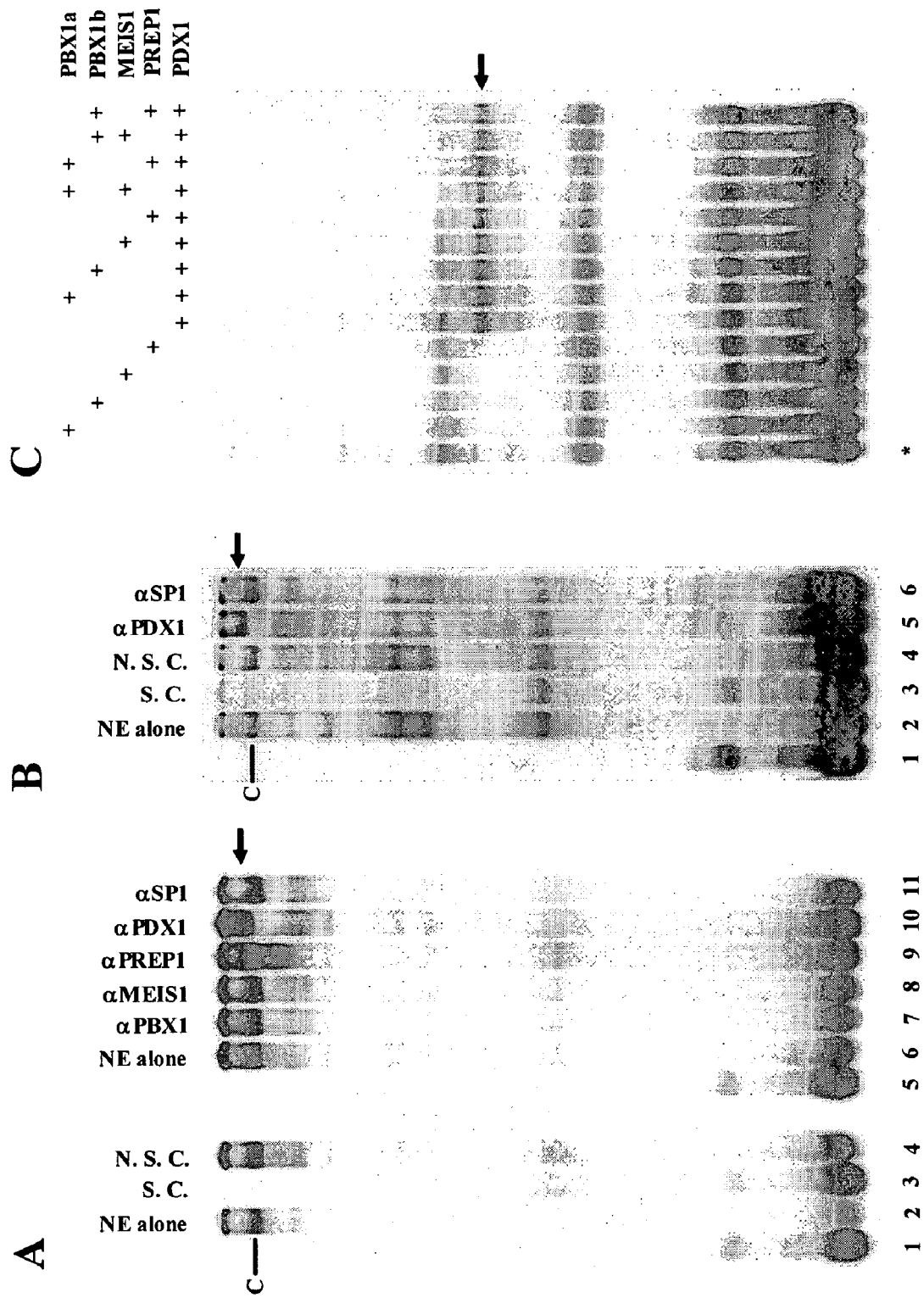

FIGS. 2A–2C show PDX1 binding to the 45-bp CMV element. (A) EMSA (electrophoretic mobility shift assay) was performed using nuclear extracts of 293 cells and radiolabeled CMV1 DNA probe containing the first 23 bases of the 45-bp region of interest (i.e. 5'-TGATTATTGAC-TAGTTATTAATA; SEQ ID NO: 5). Lanes 1 and 5 contained the DNA probe alone whereas the probe and nuclear extracts were included in lanes 2 and 6. Lanes 3 and 4 contained either the specific (i.e. unlabeled CMV1 oligonucleotide; S.C.) or nonspecific (i.e. unlabeled SP1 consensus oligonucleotide; N.S.C.) competitor probes, respectively. "C" denotes the specific DNA-protein complex formed in the presence of CMV1 and 293 nuclear extracts. Nuclear extracts of 293 cells were incubated with antibodies against PBX1, MEIS1, PREP1, PDX1 and SP1 prior to addition of the CMV1 probe (lanes 7–10). Anti-SP1 antibodies were used as the negative control (lane 10). (B) An identical set of EMSA was performed using radiolabeled CMV2 (containing the second half of the 45-bp CMV element, 5'-GTAATCAATTACGGGGTCATTA; SEQ ID NO: 6) as the DNA probe. The position of the supershifted complex C is indicated by an arrow. (C) EMSA was carried out using the CMV1 probe and in vitro translated PBX1a, PBX1b, MEIS1, PREP1, and PDX1 proteins produced by a coupled reticulocyte lysate system. The first lane (indicated by an asterisk) contained lysates alone that did not include an expression construct, and demonstrated the binding of endogenous complexes in lysates. The arrow indicates the binding of PDX1 proteins. Similar results were obtained when the CMV2 probe was used.

Figure 3:
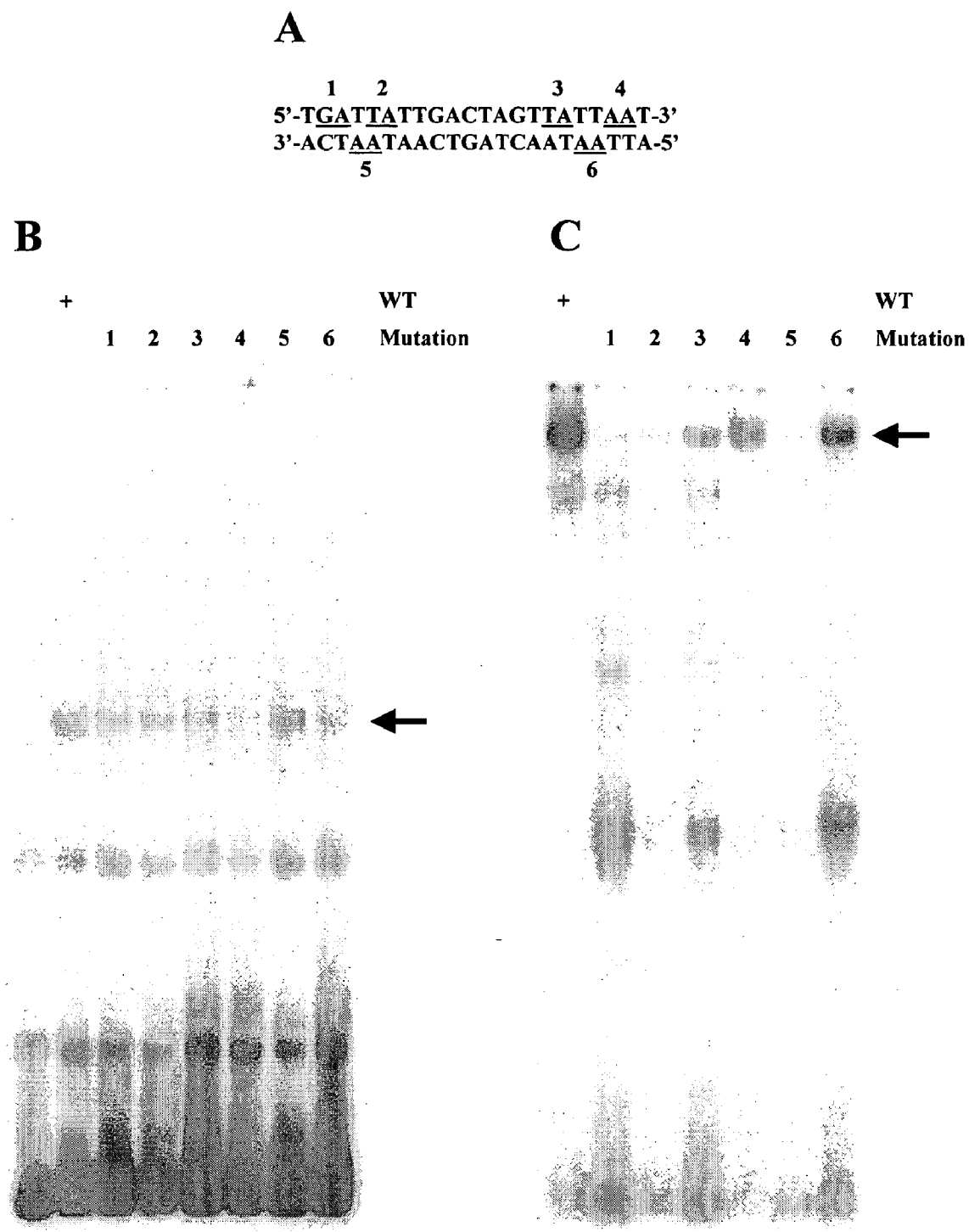

FIGS. 3A–3C show identification of PDX1 binding sites in CMV1. (A) Potential PDX1 binding motifs present within CMV1 DNA (SEQ ID NOs: 7 and 8) are indicated, including three TAATs, two TTATs, and one TGAT. Six individual mutant CMV1 oligonucleotides were generated, each destroying a specific possible PDX1-binding tetramer (position 1 to 6). For each mutant, the middle two nucleotides of the tetramers were changed to two cytosines (underlined). (B) EMSA was carried out utilizing a wild-type (WT) or mutated oligonucleotide (Mutation 1 to 6) combined with in vitro translated PDX1 proteins. The first lane contained the WT CMV1 DNA probe and lysates without the Pdx1 expression plasmid whereas the PDX1 proteins were included in the remaining lanes. The complexes containing PDX1 proteins are indicated by an arrow. (C) 293 nuclear extracts and the indicated CMV1 probe (WT or Mutation 1 to 6) were included in the EMSA. The position of the CMV1-protein complex is indicated by an arrow.

Figure 4:
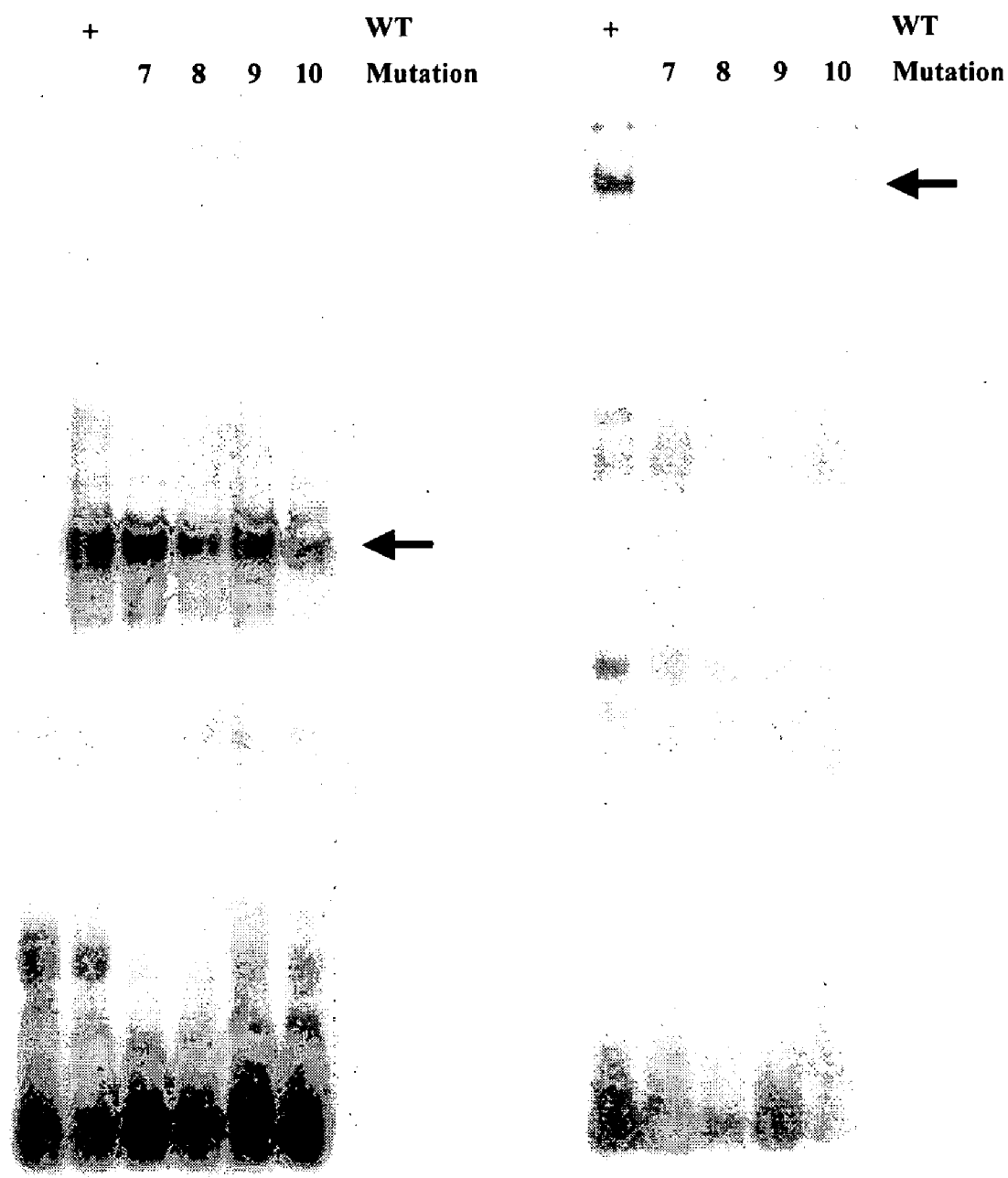

FIGS. 4A–4C show identification of PDX1 binding sites in CMV2. (A) Four potential PDX1 binding motifs are present within CMV2 DNA (SEQ ID NOs: 9 and 10), including three TAAT and one TGAT tetramers. Four individual mutant CMV2 oligonucleotides were generated, each of which destroyed a specific possible PDX1 tetramer (position 7 to 10). The middle two nucleotides of the tetramers were changed to two cytosines (underlined). (B) EMSA was performed using a wild-type (WT) or mutated oligonucleotide (Mutation 7 to 10) and the in vitro translated PDX1 proteins. The first lane contained the WT CMV2 DNA and lysates without the Pdx1 expression plasmid whereas the PDX1 proteins were included in the remaining reactions. The binding of PDX1 proteins is indicated by an arrow. (C) EMSAs were performed with nuclear extracts prepared from 293 cells and the indicated CMV2 nucleotide (WT or Mutation 7 to 10). The position of the CMV2-protein complex is indicated by an arrow.

Figure 5:
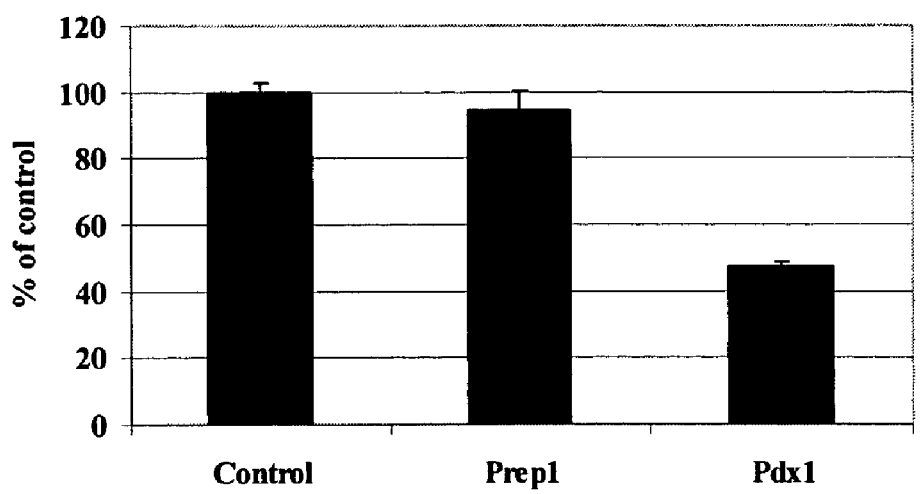
Figure 5:
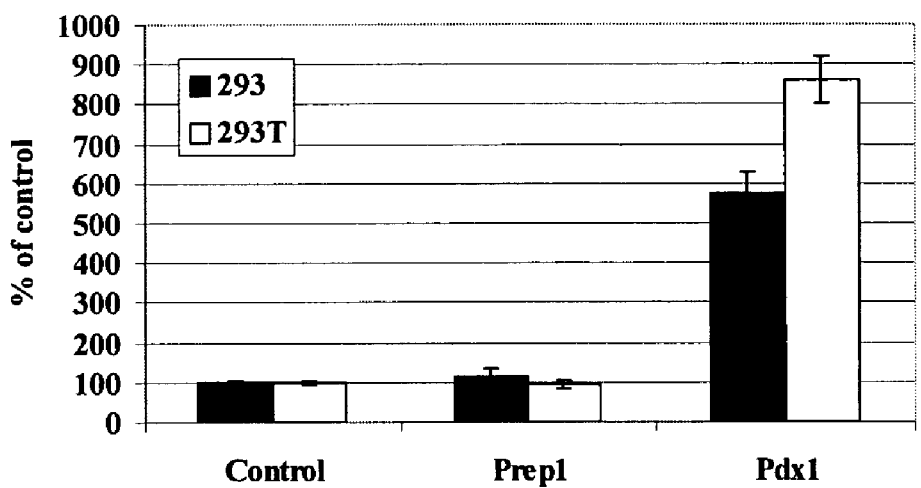
Figure 5:
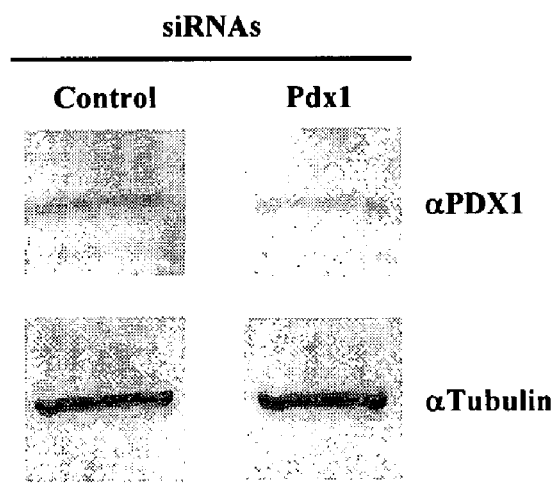

FIGS. 5A–5C show PDX1 repression of the transcription from the human CMV IE promoter. (A) PDX1 overexpression assays. 293 cells were co-transfected with the human CMV-R-Luc reporter vector and an expression plasmid, pUB-β-Gal, pUB-Prep1, or pUB-Pdx1. pUB-β-Gal served as a negative control. pUB-F-Luc was used as an internal control to normalize for transfection efficiency. *Renilla* and firefly luciferase activities were then measured. (B) PDX1 knock-down assays. 293 or 293T cells were co-transfected with human CMV-Luc and a siRNA directed against *Renilla* luciferase, Prep1, or Pdx1. The siRNA of *Renilla* luciferase served as a control. (C) The effects of Pdx1 siRNA on PDX1 protein synthesis. 293 cells were transfected with a siRNA against firefly luciferase or Pdx1 for 36–48 hours. The siRNA of firefly luciferase was used as a negative control. The cell lysates were analyzed by western blot using anti-PDX1 antibodies. γ-tubulin was used as the loading control.

Figure 6:
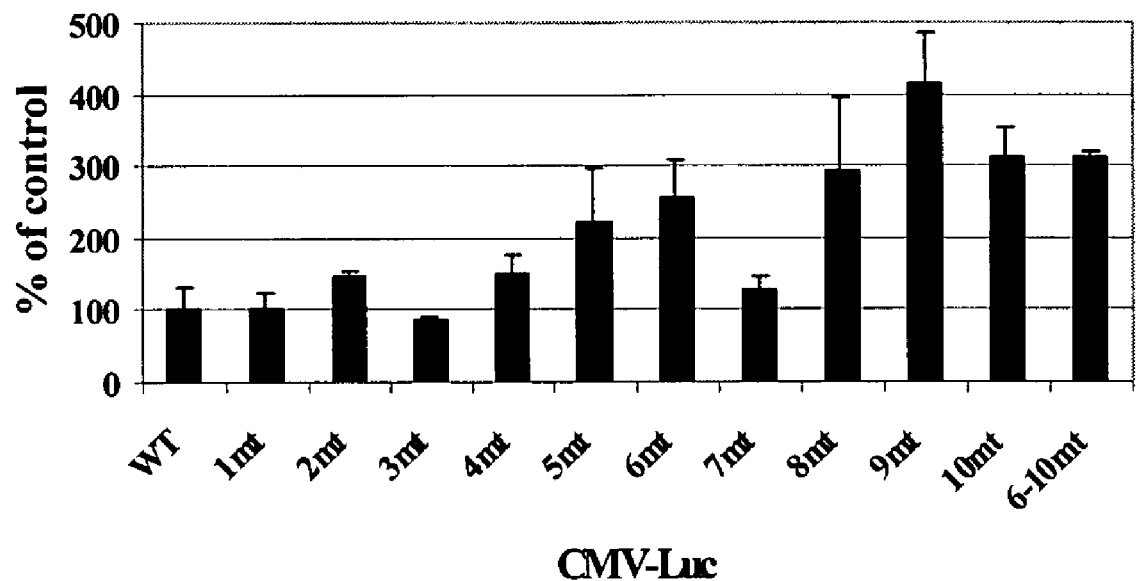

FIGS. 6A–6B show effects of the mutant PDX1 sites on human CMV IE transcription. (A) Ten individual CMV-Luc mutant plasmids were generated which contained mutations in one of the ten confirmed or putative PDX1 binding sites within the 45-bp CMV element (SEQ ID NOs: 11 and 12). The individual mutated sites are underlined. (B) 293T cells were transiently transfected by a wild-type (WT) or the indicated CMV-Luc mutant plasmid (1 mt to 10 mt). Luciferase activity was measured 24–30 hours after transfection.

DETAILED DESCRIPTION OF THE INVENTION

I. Introduction

The invention is based in part on the discovery that a cellular homeoprotein, PDX1, functions as a transcriptional repressor of the immediate early (IE) gene of human cytomegalovirus (CMV). The IE gene expression is the key to latency and active replication due to their transactivating and repressing functions. The present inventors discovered that a specific 45-bp element, which spans from nucleotide −593 to −549 of the CMV IE promoter, demonstrated varying degrees of PDX1 binding by EMSAs. In cell-based reporter gene assays, ectopic expression of PDX1 resulted in greater than 50% reduction in CMV IE-dependent luciferase activity, whereas PDX1 knockdown by siRNA caused a 6- to 9-fold increase in transcription. Furthermore, an increase in CMV IE promoter activity was observed when the PDX1 DNA-binding motifs were mutated.

The importance of this unique region in human CMV IE transcription and viral replication has been known in the art. The IE gene products, IE1 and IE2, have been shown to be required for initiating viral replication (Marchini et al., J. Virol. 75:1870–1878, 2001; and Greaves et al., J. Virol. 72:366–379, 1998). A deletion between −521 and −579, which spans tetramers 3, 4, 6, 7, 8, 9, and 10, resulted in significant multiplicities of infection (MOI)-dependent increase in recombinant CMV replication (Meier et al., Intervirology 39:331–342, 1996). Genomes of the other herpesviruses also contain an IE gene (e.g., HSV-1) which is an important regulator of viral gene expressions. Therefore, PDX1 could also similarly inhibit replication of the other herpesviruses.

In accordance with these discoveries, the present invention provides methods for identifying agents that enhance PDX1-mediated transcription repressing activity and thus inhibit replication of herpesviruses (e.g., CMV) that infect human cells. This invention relies on routine techniques in the field of recombinant genetics. Basic texts disclosing the general methods to be employed in the invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994). The following sections provide further guidance for making and using the compositions of the invention, Sand for carrying out the methods of the invention.

II. Definition

Unless defined otherwise, all technical and scientific terms used herein have the same meaning as commonly understood by those of ordinary skill in the art to which this invention pertains. The following references provide one of skill with a general definition of many of the terms used in this invention: Singleton et al., *Dictionary of Microbiology and Molecular Biology* (3d ed. 2002); the *Larousse Dictionary of Science and Technology* (Walker ed., 1995); and the *Collins Dictionary of Biology* (2d ed. 1999). In addition, the following definitions are provided to assist the reader in the practice of the invention.

A "full length" PDX1 protein or Pdx1 polynucleotide refers to a polypeptide or polynucleotide, or a variant thereof, that contains all of the elements normally contained in one or more naturally occurring, wild type Pdx1 polynucleotides or PDX1 polypeptides. It will be recognized, however, that derivatives, homologs, and fragments of a PDX1 that modulate a herpesvirus (e.g., human CMV) replication can be readily used in the present invention.

The term "inhibiting replication of a herpesvirus that infects human cells" as used herein refers to inhibition of any process in human herpesvirus replication. The term includes, but is not limited to, processes such as transcription of herpesviral genes. Other processes that may be involved in the replication of herpesvirus include viral integration, RNA processing, and assembly of virus particles. Typically, the methods of the invention identify modulators that inhibit herpesviral gene transcription.

"Modulators" refer to molecules that enhance the ability of PDX1 to suppress replication of a herpesvirus (e.g., CMV) that infects human cells. Typically, such modulators promote or enhance transcriptional repression mediated by PDX1. Modulators include naturally occurring and synthetic compounds. Samples or assays comprising a PDX1 polypeptide or Pdx1 nucleic acid sequence and a test compound as described herein are treated with a potential modulator and are compared to control samples without the modulator to examine the extent of effect. Control samples (not treated with modulators) are assigned a relative activity value of 100%. Modulation of PDX1 activity is achieved when the activity (e.g., transcriptional repression activity) compared to the control is more than about 20%, optionally 50%, or 100%, 200%, 500% or more.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605–2608 (1985); and Cassol et al. (1992); Rossolini et al., Mol. Cell. Probes 8:91–98 (1994)).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The terms "identical" in the context of two or more PDX1 polynucleotide or polypeptide sequences, refer to two or more sequences or subsequences that are the same sequences. Two sequences are substantially identical if the two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the following sequence comparison algorithms or by manual alignment and visual inspection. The invention can employ PDX1 polypeptides or polynucleotides that are substantially identical to the human PDX1 polypeptide or Pdx1 polynucleotide, respectively, exemplified herein. Optionally, the identity exists over a region that is at least about 50 nucleotides or amino acids in length, or more preferably over a region that is 100 to 500 or 1000 or more nucleotides or amino acids in length.

Two examples of algorithms that are suitable for determining percent sequence identity and sequence similarity are the BLAST and BLAST 2.0 algorithms, which are described in Altschul et al. (1977) Nuc. Acids Res. 25:3389–3402, and Altschul et al. (1990) J. Mol. Biol. 215:403–410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff(1989) Proc. Natl. Acad. Sci. USA 89:10915) alignments (B) of 50, expectation (E) of 10, M=5, N=−4, and a comparison of both strands.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" or "expression construct" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

III. Test Compounds and General Scheme of Screening

Test compounds or candidate agents that can be employed to screen for modulators of PDX1 activity include any chemical compound (e.g., in some embodiments, small chemical compounds), or a biological entity, e.g., a macromolecule such as a protein, sugar, nucleic acid, or lipid. Thus, test compounds may be chemical molecules; combinatorial chemical libraries; nucleic acids, including oligonucleotides, anti-sense oligonucleotides, siRNAs, etc., polypeptides, including antibodies, antibody fragments, and short peptides; extracts, e.g., from natural sources; and the like.

The assays of the invention can be designed to screen large chemical libraries by automating the assay steps, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In preferred embodiments, high throughput screening methods are employed. These methods involve providing a combinatorial library, e.g., a chemical library, containing a large number of potential therapeutic compounds. Such "combinatorial chemical libraries" are then screened in one or more assays, such as transcriptional assays as described herein, to identify those library members (particular chemical species or subclasses) that display the desired characteristic activity, e.g., stimulation of PDX1-mediated transcriptional repression. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel & Sambrook, both supra), peptide nucleic acid libraries (see, e.g., U.S. Pat. No. 5,539,083), antibody libraries (see, e.g., Vaughn et al., *Nature Biotechnology*, 14(3): 309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Test compounds include numerous chemical classes, including peptides, saccharides, fatty acids, steroids, purines, pyrimidines, nucleic acids, and various structural analogs or combinations thereof. In some preferred embodiments, test compounds to be screened in the present invention are small organic molecules which generally having a molecular weight of more than about 100 and less than about 2,500 daltons. Typical small molecules are less than about 2,000, less than about 1,500, less than about 1,000, or less than about 500 daltons. The test compounds typically include functional groups necessary for structural interactions with proteins or nucleic acids, e.g., hydrogen bonding, and typically include at least an amine, carbonyl, hydroxyl, or carboxyl group, preferably at least two of the functional chemical groups. The candidate agents often comprise cyclical carbon or heterocyclic structures and/or aromatic or polyaromatic structures substituted with one or more of the above functional groups.

Employing high throughput assays of the invention, it is possible to screen thousands of different modulators in a single day. In particular, each well of a microtiter plate, e.g., a 96, 384, or 1,536-well plate, can be used to run a separate assay against a selected potential modulator, or, if concentration or incubation time effects are to be observed, every 5–10 wells can test a single modulator. Thus, a single standard microtiter plate can assay a large number of modulators. For example, if 1536-well plates are used, a single plate can easily assay from about 100–1500 different compounds. It is possible to assay many different plates, for example over 1 million wells per days, using high throughput systems, e.g., those described in WO02/31747. Thus, many thousands of compounds can be screened in a single day.

High throughput systems comprise automated components, including fluid transfer and dispensing devices. A number of fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to microtiter plates to set up several parallel simultaneous assays. Such a fluid transfer device typically comprises an array of receptacles arranged such that the outlets of the receptacle are aligned with wells on the microwell plate. The Robbins Hydra (Robbins, Scientific, Sunnyvale, Calif.) is another example of a fluid dispensing device that can also be used in high throughput screening systems. Other fluid manipulation devices may include those that incorporate positive displacement pumps and dispenser valves, such a Cartesian SynQUAD (U.S. Pat. No. 6,063,339, available from Cartesian Technologies, Inc., Irvine, Calif.).

As appreciated by one of skill in the art, the high throughput devices used in the screening methods may also comprise additional components such as an incubator, e.g., to provides particular growth conditions for cells.

Detectors may also be included in the high throughput assay system. The detectors may measure any physical property of a sample. For example, fluorescence, luminescence, phosphorescence, radioactivity, or any other physical property may be measured by the detector. Examples of detectors that are often used in cell-based high throughput screening assays include a Fluormetric Imaging Plate Reader System (FLIPR®), which is commercially available from Molecular Devices Corp. Sunnyvale, Calif.; and a chemiluminescent imaging plate reader (CLIPR™). Additional imaging systems are described, e.g., in WO00/17643.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image for high throughput systems.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. This type of apparatus is easily used for viewing any sample, e.g., by fluorescent or dark field microscopic techniques.

IV. Screening for Compounds that Bind to PDX1

To identify novel modulator of herpesviral transcription and replication, test compounds can be screened directly for ability to enhance PDX1-mediated transcriptional repression of herpesviral genes. Alternatively, test compounds are also examined for their ability to bind to PDX1, and the binding assays are typically performed in conjunction with transcription assays. The binding and transcription assays may be performed in either order. In some embodiments, test compounds are first screened with a binding assay. Such pre-screening allows identification of compounds that specifically bind to a PDX1 polypeptide. These compounds can then be used to identify modulators that enhance transcription repressing activity of PDX, as detailed below.

PDX1 is also termed insulin promoter factor 1 (IPF-1). Polynucleotide and amino acid sequences encoding PDX1 from human and other animals are known and publicly available, e.g., Marshak et al., Proc. Natl. Acad. Sci. U.S.A. 93: 15057–15062, 1996 (human PDX1); Ohlsson et al., EMBO J. 12: 4251–4259, 1993 (mouse PDX1); Leonard et al., Mol. Endocrinol. 7: 1275–1283, 1993 (rat PDX1); and Milewski, Endocrinology 139: 1440–1449, 1998 (zebrafish PDX1). For example, human PDX1 amino acid and nucleic acid sequences are available under accession numbers CAA68169 and X99894, respectively; and murine PDX1 amino acid and nucleic acid sequences are available under accession numbers NP_032840 and NM_008814, respectively.

In some embodiments, the PDX1 polypeptide used in the methods of the invention is a fragment or domain that essentially consists of, at least 15, often at least 20, 30, 40, or 50, 100 or more contiguous amino acids of a PDX1 protein having the amino acid sequence of one of the exemplary sequences provided above. Alternatively, the PDX1 polypeptides may have 60% identity, more often at least 70%, 80%, 85%, 90%, 95%, or greater identity to an exemplary PDX1 amino acid sequence.

PDX1 polypeptides for use in this invention include fragments and variants that retain the ability to repress transcription of genes that are under the control of a PDX1 response element. PDX1 response elements are usually transcription regulatory elements that are recognized by PDX1, e.g., an upstream transcription regulatory element of the IE gene of a herpesvirus that infect human cells. In some embodiments, the −593 to −549 region upstream of the transcription start site of the CMV IE gene (SEQ ID NO: 1) can be used, as exemplified in the Examples below. The activity can be tested using assays well known to those of skill in the art. For example, a transcription assay that measures the ability of a PDX1 polypeptide to repress a reporter gene expression under the control of a PDX1 response element can be used to identify PDX1 proteins for use in the invention. Those PDX1 polypeptide variants or fragments that exhibit at least 50%, often 80%, 90%, 100% or greater activity relative to a reference PDX1, e.g., human or mouse PDX1, are typically used in the screening methods of the invention.

Either naturally occurring or recombinant PDX1 polypeptides can be purified for use in the assays of the invention. Natural occurring PDX1 polypeptides can be purified from any source. Recombinant polypeptides can be purified from any suitable expression system. The polypeptides may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A PDX1 polypeptide can then be used in a binding assay to identify test compounds that bind to the polypeptide. Binding of test compounds to a PDX1 polypeptide can be assayed by a number of methods including e.g., labeled in vitro protein-protein binding assays, electrophoretic mobility shift assays, immunoassays for protein binding, functional assays (phosphorylation assays, etc.), and the like. See, e.g., U.S. Pat. Nos. 4,366,241; 4,376,110; 4,517,288; and 4,837,168; and also Bevan et al., Trends in Biotechnology 13:115–122, 1995; Ecker et al., Bio/Technology 13:351–360, 1995; and Hodgson, Bio/Technology 10:973–980, 1992. The test compounds can be identified by detecting a direct binding to the PDX1 polypeptide, e.g., co-immunoprecipitation with the PDX1 polypeptide by an antibody directed to the PDX1 polypeptide. The test compound can also be identified by detecting a signal that indicates that the agent binds to the PDX1 polypeptide, e.g., fluorescence quenching.

Competition assays provide a suitable format for identifying test compounds that specifically bind to a PDX1 polypeptide. In such formats, test compounds are screened in competition with a compound already known to bind to the PDX1 polypeptide. The known binding compound can be a synthetic compound. It can also be an antibody, which specifically recognizes the PDX1 polypeptide, e.g., a monoclonal antibody directed against the PDX1 polypeptide. If the test compound inhibits binding of the compound known to bind the PDX1 polypeptide, then the test compound also binds the PDX1 polypeptide.

Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242–253 (1983)); solid phase direct biotin-avidin EIA (see Kirkland et al., J. Immunol. 137:3614–3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using $^{125}I$ label (see Morel et al., Mol. Immunol. 25(l):7–15 (1988)); solid phase direct biotin-avidin EIA (Cheung et al., Virology 176:546–552 (1990)); and direct labeled RIA (Moldenhauer et al., Scand. J. Immunol. 32:77–82 (1990)). Typically, such an assay involves the use of purified polypeptide bound to a solid surface or cells bearing either of these, an unlabelled test compound and a labeled reference compound. Competitive inhibition is measured by determining the amount of label bound to the solid surface or cells in the presence of the test compound. Usually the test compound is present in excess. Test compounds identified by competition assay include compounds binding to the same epitope as the reference compound and compounds binding to an adjacent epitope sufficiently proximal to the epitope bound by the reference compound for steric hindrance to occur. Usually, when a competing agent is present in excess, it will inhibit specific binding of a reference compound to a common target polypeptide by at least 50 or 75%.

The screening assays can be either in insoluble or soluble formats. One example of the insoluble assays is to immobilize the PDX1 polypeptide or its fragments onto a solid phase matrix. The solid phase matrix is then put in contact with test compounds, for an interval sufficient to allow the test compounds to bind. After washing away any unbound material from the solid phase matrix, the presence of the compound bound to the solid phase allows identification of the compound. The methods can further include the step of eluting the bound compound from the solid phase matrix, thereby isolating the compound. Alternatively, other than immobilizing the PDX1 polypeptide, the test compounds are bound to the solid matrix and the PDX1 polypeptide molecule is then added.

Soluble assays include some of the combinatory libraries screening methods described above. Under the soluble assay formats, neither the test compounds nor the PDX1 polypeptide are bound to a solid support. Binding of a PDX1 polypeptide or fragment thereof to a test compound can be determined by, e.g., changes in fluorescence of either the PDX1 polypeptide or the test compounds, or both. Fluorescence may be intrinsic or conferred by labeling either component with a fluorophor.

In some embodiments, test compounds may be assayed for the ability to enhance or disrupt PDX1 interactions with proteins with which it forms complexes, e.g., homeodomain proteins such as PBX1. For example, a test compound can be added, either before, after, or concurrently, to binding reaction comprising PDX1 and PBX1. Modulation (e.g., stimulation) of the PDX1 binding interaction is achieved when the binding value deviates from that of the control by about 25%, optionally 50%, optionally 75%, 100% or more.

V. Modulation of PDX-1 Mediated Transcriptional Repression

To identify novel modulators of transcription and replication of herpesviruses (e.g., CMV), compounds that are shown to bind to PDX-1 can be further tested for ability to enhance transcription-repressing activity of PDX-1. Alternatively, test compounds can be examined directly for ability to modulate (e.g., enhance) PDX1-mediated transcriptional repression in an activity assay. Transcription levels of a reporter gene under the control of a PDX1 response element can be measured to assess the effects of a test compound on PDX1 activity. Typically, a reporter expression construct harboring a reporter gene operably linked to a PDX1 response element is employed. The PDX1 response element is typically from a herpesvirus that infects human cells, such as an upstream transcription regulatory element of the CMV IE gene. PDX1 is usually also present in the assay systems.

In in vivo assay systems, a host cell comprising the reporter construct is contacted with a test compound in the presence of a PDX1 polypeptide. The PDX1 polypeptide can be expressed endogenously in the host cells. Alternatively, it can be expressed from an expression vector that has been introduced into the host cell. The amount of time to effect potential interactions between the test compound and PDX1 may be empirically determined, such as by running a time course and measuring the level of transcription as a function of time. To identify modulators that enhance PDX1 activities, host cells containing the reporter construct are treated with a test compound, and transcription activity of the reporter gene in the host cells is then measured. As a control, transcription of the reporter gene is also determined in host cells untreated with test compounds. The amount of transcription from the treated cells is then compared to the amount of transcription in the control cells. Any difference in the amount of transcription indicates that the test compound has in some manner altered the activity of the protein of interest. For example, a positive modulator of PDX1 activity is identified if the transcription level in the treated host cells is less than 75%, optionally 50%, 25%, 10%, 5%, 1% or less, of the transcription level in the control cells.

The amount of transcription can be measured by using any method known to those of skill in the art to be suitable. For example, transcription level of a reporter gene under the control of a PDX1 response element can be examined using northern blots or PCR. In addition, expression level of the reporter molecule can be monitored by assaying the encoded polypeptide using, e.g., immunoassays. Transcription based assays using reporter genes can be used as described in the art, e.g., U.S. Pat. No. 5,436,128. The reporter genes can be, e.g., chloramphenicol acetyltransferase, luciferase, green fluorescent protein (GFP),β-galactosidase, and alkaline phosphatase.

Other than in vivo assay systems for identifying modulators of PDX1-mediated transcription, in vitro assays can also be used. In such assays, a test compound is added to an in vitro transcription reaction that measures expression of a gene that is regulated by PDX1 (e.g., the CMV IE gene) or a reporter gene under the control of a PDX1 response element. Typically, a PDX1 polypeptide is also present in the reaction in order to assess the ability of a test compound to modulate (e.g., enhance) PDX1-mediated transcriptional repression.

Expression vectors that express a PDX1 polypeptide and reporter gene under the control of a PDX1 response element can be generated using procedures well known in the art (see, e.g., Sambrook et al., and Ausubel et al., both supra). The cellular transcription assays can be performed using any host cell that can support transcription of PDX1 and the reporter gen. Examples of suitable cell lines include HEK 293 cells and 293T cells as discussed in the Examples below. Additional cell lines that may be employed include HCT116 cells, MCF-7 cells, Hela cells, and HepG2 cells.

VI. Therapeutic Applications

The present invention provides compositions and methods for treating infections of herpesviruses in various subjects including human. There are a number of diseases and conditions that are mediated by or associated with herpesviruses. For example, human CMV is associated with infectious mononucleosis. Infection by human herpesvirus 6 & 7 leads to mild early childhood roseola. Herpes simplex virus 1 causes facial, labial and ocular lesions, while herpes simplex virus 2 is associated with genital lesions. Varicellazoster virus (human herpesvirus 3) is implicated in chickenpox and shingles. Epstein-Barr virus (human herpesvirus 4) is a cofactor in human cancers, and Karposi's sarcoma herpesvirus (human herpesvirus 8) is a cofactor in Karposi's sarcoma.

Human CMV is also a common cause of mental retardation in children who acquire the infection in utero from mothers carrying an active infection. In addition, some newborn infants carry CMV and the virus can cause severe congenital disease in the fetus or infant. Inhibiting or modulating the IE expression and/or function has been suggested in the art as novel strategy of treating herpesvirus (e.g., CMV) associated diseases (see, e.g., Scholz et al., Antiviral Res. 49: 129–145, 2001). All the diseases and conditions discussed above can be treated with the novel modulators of the present invention which enhance PDX1-mediated transcriptional repression of the IE gene.

Modulators that enhance or stimulate PDX1 activity can be administered directly to a subject (e.g., a human) that is infected by a herpesvirus (e.g., CMV). The modulators can be administered alone or as the active ingredient of a pharmaceutical composition. Administration can be by any of the routes which are well known to those of skill in the art and which are normally used for introducing a modulating compound into ultimate contact with the tissue to be treated.

The identified stimulator of PDX1-mediated transcriptional repression can be administered to a patient at therapeutically effective doses to prevent, treat, or control herpesviral disease, e.g., CMV infection. The compounds are administered to a patient in an amount sufficient to elicit an effective protective or therapeutic response in the patient. An effective protective or therapeutic response is a response that at least partially arrests or slows the symptoms or complications of the disease. An amount adequate to accomplish this is defined as "therapeutically effective dose." The optimal dose level for any patient will depend on a variety of factors including the efficacy of the specific modulator employed, the age, body weight, physical activity, and diet of the patient, and on a possible combination with other drug. The size of the dose also will be determined by the existence, nature, and extent of any adverse side-effects that accompany the administration of a particular compound or vector in a particular subject.

In determining the effective amount of the modulator to be administered, a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side-effects of the modulator at various concentrations, as applied to the mass and overall health of the subject. Administration can be accomplished via single or divided doses.

The modulators of the invention may be used alone or in conjunction with other agents that are known to be beneficial in treating or preventing human diseases that are mediated by herpesviruses, e.g., CMV-1 infection. The modulators of the invention and another agent may be co-administered, either in concomitant therapy or in a fixed combination, or they may be administered at separate times.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington: The Science and Practice of Pharmacy, Mack Publishing Co., 20$^{th}$ ed., 2000).

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, intrathecally or into the eye (e.g., by eye drop or injection). The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

Pharmaceutically acceptable carriers are determined in part by the particular composition being administered, as well as by the particular method used to administer the composition. Accordingly, there are a wide variety of suitable formulations of pharmaceutical compositions of the present invention, as described below (see, e.g., Remington. The Science and Practice of Pharmacy, Mack Publishing Co., 20$^{th}$ ed., 2000).

EXAMPLES

Example 1

General Methods

This example describes materials and methods used to show that PDX1 represses CMV-dependent transcription.

Plasmids and plasmid construction. The Pdx1 (accession number: X99894) complementary DNA (cDNA) was reverse transcribed with gene specific primers using the Qiagen OneStep RT-PCR (reverse transcription-PCR) kit as prescribed by the manufacturer. In brief, the cDNA product was synthesized and amplified from 1 μg purified human pancreatic polyA mRNA (Clontech) using two primers: 5'-AATAGGATCCGCCGCAGCCATGAACGGCGA (SEQ ID NO: 13 and 5'-CTCCTCTAGACTCTCATCGTGGT TCCTGCG (SEQ ID NO: 14). The resultant product was inserted into the multiple cloning site of pUB6/V5-His B (Invitrogen) using the appended BamHI and XbaI (underlined) restriction sites to generate pUB-PDX1, in which the expression of Pdx1 was driven by the human ubiquitin C promoter. A pUB-PREP1 plasmid was generated by cloning the coding sequences of Prep1 into the pUB6 vector using CMV-PREP1 as the DNA template. The pUB-β-Gal plasmid was purchased from Invitrogen. The pCITE-PBX1a, pCITE-MEIS1, and pCITE-PREP1 plasmids were constructed as described previously. The pCITE-PBX1b and pCITE-PDX1 plasmids were created by cloning the coding regions of Pbx1b and Pdx1 into pCITE vectors using CMV-PBX1b and pUB-PDX1 as templates. The pCITE constructs were used to synthesize translated proteins in vitro using TNT Quick Coupled Transcription/Translation Systems (Promega). Three luciferase plasmids were used in this study: ubiquitin-firefly luciferase (pUB-F-Luc), CMV-firefly luciferase (CMV-F-Luc; containing the human CMV IE promoter-enhancer), and CMV-*Renilla* luciferase (CMV-R-Luc; containing the human CMV IE promoter-enhancer). The firefly luciferase sequences of pGL2 control (Promega) were subcloned into pUB6 or pcDNA6 (Invitrogen) to generate pUB-F-Luc or CMV-F-Luc. CMV-R-Luc was purchased from Promega (i.e. pRL-CMV). Mutations and deletions of the human CMV IE promoter were constructed using the QuickChange Site-Directed Mutagenesis Kit (Stratagene). All the CMV-Luc mutants were generated using CMV-R-Luc as template. To mutate the potential homeobox binding tetramer, the middle two nucleotides were changed to two cytosines (for example, T<u>AA</u>T to T<u>CC</u>T).

EMSAs. The 45-nucleotide CMV sequences (underlined, see below) were divided into two halves, CMV1 (5'-GGCAT <u>TGATTATTGACTAGTTATTAATAGTAA</u>) (SEQ ID NO: 15) and CMV2 (5'-AATA<u>GTAATCAATTACGGGGTCA TTA</u>GTTCA) (SEQ ID NO: 16). Electrophoretic mobility shift assays (EMSAs) were then performed using CMV1 or CMV2 as the DNA probes. Briefly, anti-PBX1, anti-MEIS1, anti-PREP1, anti-PDX1, anti-HOXA9 or anti-SP1 antibodies (Santa Cruz Biotechnology, Inc.) were incubated with nuclear extracts prepared from 293 or HeLa cells for 10 min at room temperature before the $^{32}$P-labeled probe was included. When in vitro translated proteins were used in EMSAs, DNA binding reactions were performed at 4° C. for 30 minutes. DNA and DNA-protein complexes were resolved on 5% non-denaturing polyacrylamide gels at room temperature in 0.3×TBE (27 mM Tris-Borate, pH 8.3, 0.6 mM EDTA). Following electrophoresis, the gels were dried and exposed to X-ray film.

Transfection and luciferase assays. 293 or 293T cells were grown to 50–80% confluence in 96-well plates. Transfections were performed using Fugene 6 (Roche) or LipofectAmine 2000 Reagent (Invitrogen) as described in the manufacturer's manuals. For the overexpression assays, 293 cells were co-transfected with CMV-R-Luc, the indicated expression vectors (i.e. pUB-PDX1, -PREP1, or -β-Gal) and a pUB-F-Luc internal control plasmid for 48 hours. In the CMV mutant assays, 293 and 293T cells were co-transfected with pUB-F-Luc (as internal control) and a wild-type or mutant CMV-R-Luc. Firefly and *Renilla* luciferases were measured using the Dual-Glo assay system (Promega) and the activities were determined using an Acquest multimode reader (LJL Biosystems, Inc.). A short interfering RNA (siRNA) targeting positions 554–572 after the start codon of Pdx1 and a Prep1 siRNA corresponding to region 20–38 after the start codon of Prep1 (accession number: XM_033008) were purchased from Qiagen. The fluorescein labeled luciferase GL2 duplex used to determine transfection efficiency was obtained from Dharmacon. The siRNA targeting *Renilla* luciferase was used as a control. The inhibitory effects of the Pdx1 and Prep1 siRNAs on cellular PDX1 and PREP1 protein synthesis were examined by western blot analysis using anti-PDX1 and anti-PREP1 antibodies (Santa Cruz Biotechnology, Inc.). 293 and 293T cells were co-transfected with CMV-F-Luc and the indicated siRNA (i.e. Pdx1, Prep1, or R-Luc siRNAs). Firefly luciferase activities were measured by the Bright-Glo assay system (Promega) 48 hours after transfection.

Example 2

PDX1 and Transcriptional Regulation of the Human CMV IE Gene

Figure 1:
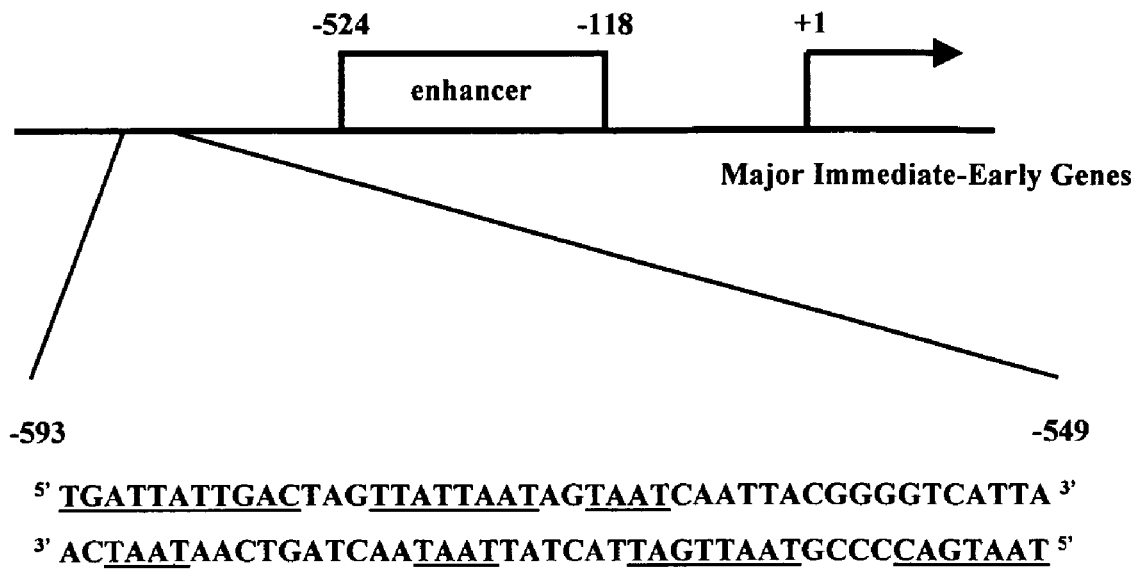
FIGS. 1A–1B show the 45-bp human CMV element containing twelve putative homeobox protein binding sites.

This example describes the analysis of the promoter-enhancer regions of human CMV IE gene for consensus homeoprotein binding elements. A 45-nucleotide fragment located at position −593 to −549 upstream of the transcription start site of the CMV IE gene was found to contain numerous putative homeoprotein binding sites (FIG. 1A). Including the reverse complementary sequences, 12 potential tetramer binding sites for homeobox proteins were identified, including two PBX1 (i.e. TGAT), two PREP1 or MEIS1 (i.e. TGAC), six PDX1 (i.e. TAAT) and eight HOX binding sites (i.e. TAAT or TTAT) (FIG. 1A). A previous study indicated that a PDX binding site, AGATAAATGAG, located in the B element of the transcriptional enhancer of the pancreatic elastase I gene (Ela1), shares significant similarity with the first 11-bp of the CMV 45 nucleotide-fragment (FIG. 1B). It has been shown that PDX1 associates with the B element by forming a trimeric complex with PBX1b and MEIS2 in pancreatic acinar cell lines, whereas PDX1 binds to the B element alone in β-cell lines. It has additionally been observed that cooperative interactions occur between PBX1, PREP1, and PDX1 on the somatostatin mini-enhancer. Based on these observations, we performed EMSAs to examine the possible association between the 45-bp CMV DNA and homeobox proteins, including PBX1, MEIS1, PREP1, and PDX1.

The 45-bp CMV DNA was divided into two segments extending from position −593 to −571 (CMV1) and from position −570 to −549 (CMV2). Incubation of $^{32}$P-labeled CMV1 DNA with nuclear extracts prepared from 293 cells resulted in the formation of a major DNA-protein complex, complex C (FIG. 2A; indicated as "C"). The specificity of the complex for CMV1 binding was confirmed using unlabeled specific competitor oligonucleotides (i.e. unlabeled CMV1; FIG. 2A, lane 3). No effects on the complex were observed in the presence of an unlabeled nonspecific competitor (i.e. SP1 consensus oligonucleotide; FIG. 2A, lane 4).

The interaction between the CMV1-region and the associated protein complex was then examined using antibodies specific to the individual homeobox proteins. Incubation of nuclear extracts with antibodies raised against PDX1 proteins resulted in the appearance of a supershifted complex (FIG. 2A; arrow). However, the incubation of nuclear extracts with antibodies against PBX1, MEIS1, or PREP1 proteins did not produce any significant new species (FIG. 2A). A parallel set of EMSAs performed using CMV2 as the DNA probe yielded the same complex C as indicated in FIG. 2A. The further addition of anti-PDX1 antibodies to the reaction mixture resulted in a supershift of complex C (FIG. 2B; arrow). No effects on the DNA-protein complex were seen using anti-PBX1, MEIS1 or PREP1 antibodies. When the same EMSAs (CMV1 and CMV2 as DNA probes) were performed using nuclear extracts prepared from HeLa cells, instead of 293 cells, identical results were obtained. In agreement with our findings using 293 nuclear extracts, the supershifted C complex was observed only when anti-PDX1 antibodies were included in the reaction.

It has been shown that HOXA9 can form a trimeric protein complex with PBX1-MEIS1 or PBX1-PREP1. Since there are eight potential HOX binding sites present in the 45-bp CMV region, we investigated the possible association between HOXA9 proteins and the CMV DNA element. EMSAs were thus performed, incubating anti-HOXA9 antibodies with nuclear extracts. The presence of HOXA9 antibodies did not, however, affect the formation of the CMV DNA-protein complex.

To further validate the EMSA data using nuclear extracts and antibodies, we also performed EMSAs using in vitro translated PBX1a, PBX1b, MEIS1, PREP1, HOXA9, and PDX1 proteins. The results showed that only the PDX1 protein was able to bind to the CMV1 DNA probe (FIG. 2C). PDX1 further did not appear to cooperate with the other homeobox proteins in associating with CMV1 (FIG. 2C). Furthermore, the complex of CMV1-PDX1 (FIG. 2C) was much smaller than that of CMV1-protein in the EMSAs using nuclear extracts (FIG. 2A), suggesting that other cellular proteins are also present in the CMV1-protein complexes. An identical set of results was obtained when CMV2 was used as the DNA probe). Lastly, HOXA9 did not appear to interact with the CMV DNA either as a monomer, or in combination with the other homeoproteins as a dimer (i.e. PBX1-HOXA9, MEIS1-HOXA9, or PREP1-HOXA9), or a trimer (i.e. PBX1-MEIS1-HOXA9 or PBX1-PREP1-HOXA9). Collectively, these gel shift experiments indicate that PDX1 protein is included in the CMV-protein complexes, which contain multiple cellular proteins.

Example 3

Identification of PDX1 Binding Sites

This example describes identification of the exact PDX1 binding site within the 45-bp CMV region. There are six putative PDX1 binding tetramers, TAAT, present in the region (FIG. 1A). Of note, there are also two TTAT and two TGAT tetramers that contain a mismatch at a single position and could therefore be homeobox binding sites. To determine which tetramer conferred association with PDX1, point mutations at each of the ten potential PDX1 sites (i.e., TAAT, TTAT, and TGAT) were generated, by changing the central two nucleotides to two cytosines. Six possible PDX1 sites are present in CMV1 (tetramer 1 to 6; FIG. 3A) and four in CMV2 (tetramer 7 to 10; FIG. 4A). EMSAs were thus performed using in vitro synthesized PDX1 protein and a wild-type or site-mutated CMV1 DNA probe. As shown in FIG. 3B, although mild binding-loss effects were observed for mutations at each site, mutations at tetramers 4 and 6 (both are TAAT) and to a lesser extent, tetramer 3 (i.e. TTAT), prevented PDX1 binding, suggesting that PDX1 binds to these regions preferentially over sites 1, 2, and 5. The correlation between PDX1 binding elements and the formation of CMV1-protein complexes was also examined. The same experiments were performed as described above using 293 nuclear extracts instead of PDX1 protein in the assays. All six mutations caused different levels of disruption to the formation of CMV1 DNA-protein complexes (FIG. 3C). However, the most significant effects were seen when tetramers 1, 2, or 5 were mutated, resulting in a near complete disruption of the DNA-protein complexes (FIG. 3C).

A similar approach was utilized to examine the potential PDX1 binding motifs in the CMV2 nucleotides (FIG. 4A). Only slight effects on PDX1-CMV2 complexes were observed when sites 7–9 were changed (FIG. 4B). On the other hand, a significant reduction in PDX1 binding was detected when a mutation was introduced into site 10 (which was TAAT), suggesting that PDX1 binds to site 10 versus tetramers 7, 8 and 9 (FIG. 4B). The effects of these 4 mutations on the formation of CMV2-protein complexes in 293 nuclear extracts were examined next. The results indicate that all four mutations caused complete disruption of DNA-protein complex formation (FIG. 4C). Collectively, in experiments with PDX1 protein alone, three TAAT sites (site 4, 6, and 10) were identified as major PDX1 binding motifs in contrast to the other three TAAT sites (site 5,.7, and 9; FIGS. 3B and 4B). In addition, the data using nuclear extracts showed that PDX1 is likely not the only determinant in the formation of these CMV DNA-protein complexes (FIGS. 3C and 4C). It is possible that the other unknown cellular proteins present in the CMV-protein complexes might also participate in CMV DNA binding and the formation of the complexes.

Finally, two PDX1 mutant proteins (i.e. PDX1H189F and PDX1I192Q) were employed to examine PDX1 binding sites in the CMV promoter. These proteins contain mutations within the homeodomain and fail to bind to the PDX1 DNA motif (Lu et al., Endocrinology 137: 2959–2967, 1996). These PDX1 mutants did not associate with the 45-bp region. These data reconfirmed the specific interaction between PDX1 protein and the 45-bp element.

Example 4

PDX1 is a Transcriptional Repressor of the Human CMV IE Gene

This example describes the determination that PDX1 represses transcription of human CMV IE gene. We investigated the importance of PDX1 on the transcriptional regulation of the human CMV IE gene. 293 cells were thus co-transfected with a reporter vector (CMV-*Renilla* luciferase, or CMV-R-Luc) and an expression plasmid encoding PDX1 or PREP1 (i.e., pUB-PDX1 or pUB-PREP1). The ubiquitin-firefly luciferase plasmid (i.e. pUB-F-Luc) was utilized as an internal control for normalization of transfection efficiency, whereas the pUB-β-Gal plasmid was used as a negative control. Overexpression of PDX1 resulted in a 52% decrease in CMV-dependent transcription (FIG. 5A). In agreement with the gel shift data (FIG. 2), no significant effects were observed when PREP1 was overexpressed (FIG. 5A). We also used a Pdx1 targeted siRNA to evaluate the effect of removing the PDX1 protein on CMV-mediated transcription. 293 or 293T cells were thus co-transfected with CMV-Luc and siRNAs directed against Pdx1 or Prep1. A 6 to 9-fold increase in CMV transcription was observed in the Pdx1 siRNA-transfected cells whereas no effects were detected when treating with Prep1 siRNA (FIG. 5B). The Pdx1 and Prep1 siRNAs did not cause any significant effects on cellular toxicity or proliferation as determined by Alamar Blue cell viability assays. We also generated a stable 293 cell line expressing luciferase from the human CMV IE promoter-enhancer (293-CMV-Luc cells) and performed a set of experiments identical to the ones described above. Overexpression of PDX1 caused a 30% decrease in CMV-dependent transcription. In addition, more than a 3-fold increase in luciferase activity was observed when 293-CMV-Luc cells were transfected with Pdx1 siRNA. The inhibitory effects of Pdx1 siRNA on endogenous PDX1 protein levels were confirmed by western blot analysis (FIG. 5C). A 40–50% reduction of cellular PREP1 protein was observed when cells were treated with Prep1 siRNA. The transfection efficiency of siRNA on 293 cells was determined to be around 50% using fluorescein labeled luciferase GL2 siRNA.

To further investigate the importance of PDX1 on transcriptional regulation of the CMV IE gene, mutations in each identified or putative PDX1 binding site in the promoter of CMV-Luc were generated using site-directed mutagenesis and tested for differences in expression (FIG. 6A). We used 293T cells in the assay to obtain higher transfection efficiency. 293T cells were transiently transfected with a CMV-Luc plasmid, which contained the wild-type CMV IE promoter or a mutation in the indicated PDX1 site. As shown in FIG. 6B, five mutations resulted in a greater than 2-fold induction in luciferase activity, including four TAAT tetramers (sites 5, 6, 9 and 10). Furthermore, sites 6 and 10 were identified as the major PDX1 binding sites in the EMSA experiments (FIGS. 3B and 4B). A CMV-Luc construct with double mutations at sites 6 and 10 was also generated and tested, however, no additive effects on luciferase activity were detected (FIG. 6B). Similar results were obtained when 293 cells were utilized in transfection assays. Collectively, our results indicate that PDX1 functions as a transcriptional repressor of the human CMV IE gene.

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

All publications, sequence accession numbers, patents and patent applications cited herein are hereby expressly incorporated by reference in their entirety and for all purposes as if each is individually so denoted.

We claim:

1. A method of identifying a compound that inhibits replication of a herpesvirus that infects human cells, the method comprising (a) contacting a test compound, a pancreatic-duodenal homeobox factor-1 (PDX1) polypeptide, and a reporter gene operably linked to a PDX1 response element, and (b) comparing expression level of the reporter gene in the presence of the test compound to expression level of the reporter gene in the absence of the test compound, thereby identifying a compound that inhibits replication of the herpesvirus.

2. The method of claim 1, wherein the PDX1 response element comprises a transcription regulatory sequence from the IE gene of the herpesvirus.

3. The method of claim 1, wherein the herpesvirus is human CMV.

4. The method of 3, wherein the PDX1 response element comprises nucleotides −593 to −549 of the upstream regulatory region of human CMV IE gene (SEQ ID NO: 1).

5. The method of claim 1, wherein the reporter gene and the PDX1 response element are present in an expression vector.

6. The method of claim 1, wherein the contacting is in a host cell expressing the PDX1 polypeptide.

7. The method of claim 6, wherein the PDX1 polypeptide is expressed from a second expression construct that has been introduced into the host cell.

8. The method of claim 1, wherein the reporter gene is a luciferase gene.

9. The method of claim 6, wherein the host cell is HEK 293 cell.

* * * * *

SEQUENCE LISTING

<160> NUMBER OF SEQ ID NOS: 16

<210> SEQ ID NO 1
<211> LENGTH: 45
<212> TYPE: DNA
<213> ORGANISM: Homo sapiens

-continued

```
<400> SEQUENCE: 1
tgattattga ctagttatta atagtaatca attacggggt catta                           45

<210> SEQ ID NO 2
<211> LENGTH: 45
<212> TYPE: DNA
<213> ORGANISM: Homo sapiens

<400> SEQUENCE: 2
taatgacccc gtaattgatt actattaata actagtcaat aatca                           45

<210> SEQ ID NO 3
<211> LENGTH: 14
<212> TYPE: DNA
<213> ORGANISM: Homo sapiens

<400> SEQUENCE: 3
tgattattga ctag                                                             14

<210> SEQ ID NO 4
<211> LENGTH: 14
<212> TYPE: DNA
<213> ORGANISM: Homo sapiens

<400> SEQUENCE: 4
agataaatga gttg                                                             14

<210> SEQ ID NO 5
<211> LENGTH: 23
<212> TYPE: DNA
<213> ORGANISM: Homo sapiens

<400> SEQUENCE: 5
tgattattga ctagttatta ata                                                   23

<210> SEQ ID NO 6
<211> LENGTH: 22
<212> TYPE: DNA
<213> ORGANISM: Homo sapiens

<400> SEQUENCE: 6
gtaatcaatt acgggtcat ta                                                     22

<210> SEQ ID NO 7
<211> LENGTH: 22
<212> TYPE: DNA
<213> ORGANISM: Homo sapiens

<400> SEQUENCE: 7
tgattattga ctagttatta at                                                    22

<210> SEQ ID NO 8
<211> LENGTH: 22
<212> TYPE: DNA
<213> ORGANISM: Homo sapiens

<400> SEQUENCE: 8 attataact agtcaataat ca                                                     22

<210> SEQ ID NO 9
<211> LENGTH: 21
<212> TYPE: DNA
<213> ORGANISM: Homo sapiens
```

```
<400> SEQUENCE: 9
taatcaatta cggggtcatt a                                      21

<210> SEQ ID NO 10
<211> LENGTH: 21
<212> TYPE: DNA
<213> ORGANISM: Homo sapiens

<400> SEQUENCE: 10
taatgacccc gtaattgatt a                                      21

<210> SEQ ID NO 11
<211> LENGTH: 45
<212> TYPE: DNA
<213> ORGANISM: Homo sapiens

<400> SEQUENCE: 11
tgattattga ctagttatta atagtaatca attacggggt catta            45

<210> SEQ ID NO 12
<211> LENGTH: 45
<212> TYPE: DNA
<213> ORGANISM: Homo sapiens

<400> SEQUENCE: 12
taatgacccc gtaattgatt actattaata actagtcaat aatca            45

<210> SEQ ID NO 13
<211> LENGTH: 30
<212> TYPE: DNA
<213> ORGANISM: Homo sapiens

<400> SEQUENCE: 13
aataggatcc gccgcagcca tgaacggcga                             30

<210> SEQ ID NO 14
<211> LENGTH: 30
<212> TYPE: DNA
<213> ORGANISM: Homo sapiens

<400> SEQUENCE: 14
ctcctctaga ctctcatcgt ggttcctgcg                             30

<210> SEQ ID NO 15
<211> LENGTH: 32
<212> TYPE: DNA
<213> ORGANISM: Homo sapiens

<400> SEQUENCE: 15
ggcattgatt attgactagt tattaatagt aa                          32

<210> SEQ ID NO 16
<211> LENGTH: 31
<212> TYPE: DNA
<213> ORGANISM: Homo sapiens

<400> SEQUENCE: 16
aatagtaatc aattacgggg tcattagttc a                           31
```